United States Patent
Bendahan et al.

(10) Patent No.: US 7,483,511 B2
(45) Date of Patent: Jan. 27, 2009

(54) INSPECTION SYSTEM AND METHOD

(75) Inventors: Joseph Bendahan, San Jose, CA (US); William Joseph Kelly, Coronado, CA (US); Forrest Frank Hopkins, Cohoes, NY (US)

(73) Assignee: GE Homeland Protection, Inc., Newark, CA (US)

( * ) Notice: Subject to any disclaimer, the term of this patent is extended or adjusted under 35 U.S.C. 154(b) by 5 days.

(21) Appl. No.: 11/671,042

(22) Filed: Feb. 5, 2007

(65) Prior Publication Data

US 2007/0280416 A1    Dec. 6, 2007

Related U.S. Application Data

(60) Provisional application No. 60/811,211, filed on Jun. 6, 2006.

(51) Int. Cl.
   *G01N 23/04* (2006.01)
   *H01G 1/64* (2006.01)
(52) U.S. Cl. .................. 378/57; 378/98.9
(58) Field of Classification Search ............. 378/4, 378/5, 9, 19, 51, 53, 57, 146; 250/306–308
   See application file for complete search history.

(56) References Cited

U.S. PATENT DOCUMENTS

| 6,601,022 | B2 * | 7/2003 | Zerwekh et al. ............. 702/188 |
| 6,708,140 | B2 * | 3/2004 | Zerwekh et al. ............. 702/188 |
| 7,103,137 | B2 | 9/2006 | Seppi et al. |
| 7,257,188 | B2 * | 8/2007 | Bjorkholm ................... 378/53 |
| 2004/0109532 | A1 * | 6/2004 | Ford et al. .................... 378/57 |

* cited by examiner

*Primary Examiner*—Irakli Kiknadze
(74) *Attorney, Agent, or Firm*—Richard A. DeCristofaro

(57) ABSTRACT

A method of determining a presence of items of interest within a cargo container is disclosed. The method includes obtaining information from an initial radiation scan of at least one of the cargo container and contents therein, identifying a target portion of the cargo container in response to the information obtained, transmitting a target radiation beam along the target portion of the cargo container, and detecting radiation received in response to the transmitting. The method further includes analyzing the detected radiation for a presence of items of interest, and in response to the analyzing, generating a first signal indicative of the presence of the items of interest, or generating a second signal indicative of an absence of the items of interest.

29 Claims, 3 Drawing Sheets

INSPECTION SYSTEM AND METHOD

CROSS REFERENCE TO RELATED APPLICATIONS

This application claims the benefit of U.S. provisional application No. 60/811,211, filed Jun. 6, 2006, the contents of which are incorporated by reference herein in their entirety.

BACKGROUND OF THE INVENTION

The present disclosure relates generally to detection of items of interest, and particularly to detection of contraband within cargo containers and trucks by employing radiographic means.

The modern global economy relies heavily on intermodal shipping containers for rapid, efficient transport of ocean-going cargo. However, the possibility of concealing weapons of mass destruction (WMDs) and radiological dispersal devices (RDDs) in these containers represents a potential interruption to the free flow of commerce.

Materials of concern such as uranium and plutonium that can be used to make nuclear weapons are characterized by having a high atomic number (high-Z). Similarly, radiological sources can be shielded employing high-Z materials to prevent these from being detected using passive means. Current x-ray inspection systems may not be capable to detect such materials and other items of interest such as explosives, drugs, and alcoholic beverages, and distinguish these from common materials in an expedient fashion. Accordingly, there is a need for a cargo container inspection arrangement that overcomes these drawbacks.

SUMMARY

An embodiment of the invention includes a method of determining a presence of items of interest within a cargo container. The method includes obtaining information from an initial radiation scan of at least one of the cargo container and contents therein, identifying a target portion of the cargo container in response to the information obtained, transmitting a target radiation beam along the target portion of the cargo container, and detecting radiation received in response to the transmitting. The method further includes analyzing the detected radiation for a presence of items of interest, and in response to the analyzing generating a first signal indicative of the presence of the items of interest, or generating a second signal indicative of an absence of the items of interest.

Another embodiment of the invention includes a cargo container inspection system. The system includes a processor and a support comprising an inspection cavity dimensioned so as to surround the cargo container, the support in signal communication with the processor. A radiation source is disposed upon the Support, the radiation source in signal communication with and responsive to the processor to transmit a radiation beam directed toward the cargo container. A radiation detector is disposed upon the support opposite the radiation source, the radiation detector in signal communication with the processor to detect an attenuated radiation beam in response to the transmitted radiation beam passing through the cargo container. Upon obtaining information from an initial radiation scan, the processor identifies a target portion of the cargo container and causes transmission of a target radiation beam along the identified target portion. The processor analyzes the attenuated radiation beam detected in response to the transmission of the target radiation beam to determine a presence or absence of items of interest within the cargo container and generates one of a first signal indicative of the presence of the items of interest or a second signal indicative of an absence of the items of interest.

These and other advantages and features will be more readily understood from the following detailed description of preferred embodiments of the invention that is provided in connection with the accompanying drawings.

DETAILED DESCRIPTION OF EXEMPLARY EMBODIMENTS

An embodiment of the invention provides a cargo advanced automated radiography system, also herein referred to as an inspection system, for the detection of items of interest based upon analysis of a density, shape, mass and/or atomic number of the items within a cargo container. As used herein, the phrase "cargo container" shall refer to any cargo containment means, such as intermodal cargo containers, crates or boxes within which cargo is disposed, and pallets or skids upon which cargo may be disposed and secured, for example. Further, it is contemplated that such cargo containers may be transported via any appropriate shipment mode, such as by air, sea, or land, for example. As used herein, the phrase "item(s) of interest" will represent any item shipped via cargo container that may be desired to be identified, such as explosives, weapons, drugs, cigarettes, alcohol, for example. In an embodiment, the inspection system detects items of interest having a high atomic number, also herein referred to as high Z-material, or other high-density material included to attempt to shield from detection special nuclear and radiological materials within the cargo container. As used herein, the term "high atomic number" shall refer to materials with an atomic number greater than about 57. In another embodiment, the inspection system detects items of interest based upon an unexpected density variation or gradient, such as to detect drugs, explosives or other contraband within a cargo container. In an embodiment, the inspection system performs an initial, high speed screening to localize areas of the cargo container that may include items of interest, and a second, targeted screening of the localized areas of the cargo container with an appropriate speed to provide the required discrimination of the items of interest. In an embodiment, the inspection system utilizes information from a passive portal system that detects radiation emitting from the cargo container. An embodiment includes a photo-fission interrogation to determine whether any detected high Z-material is fissile.

Figure 1:
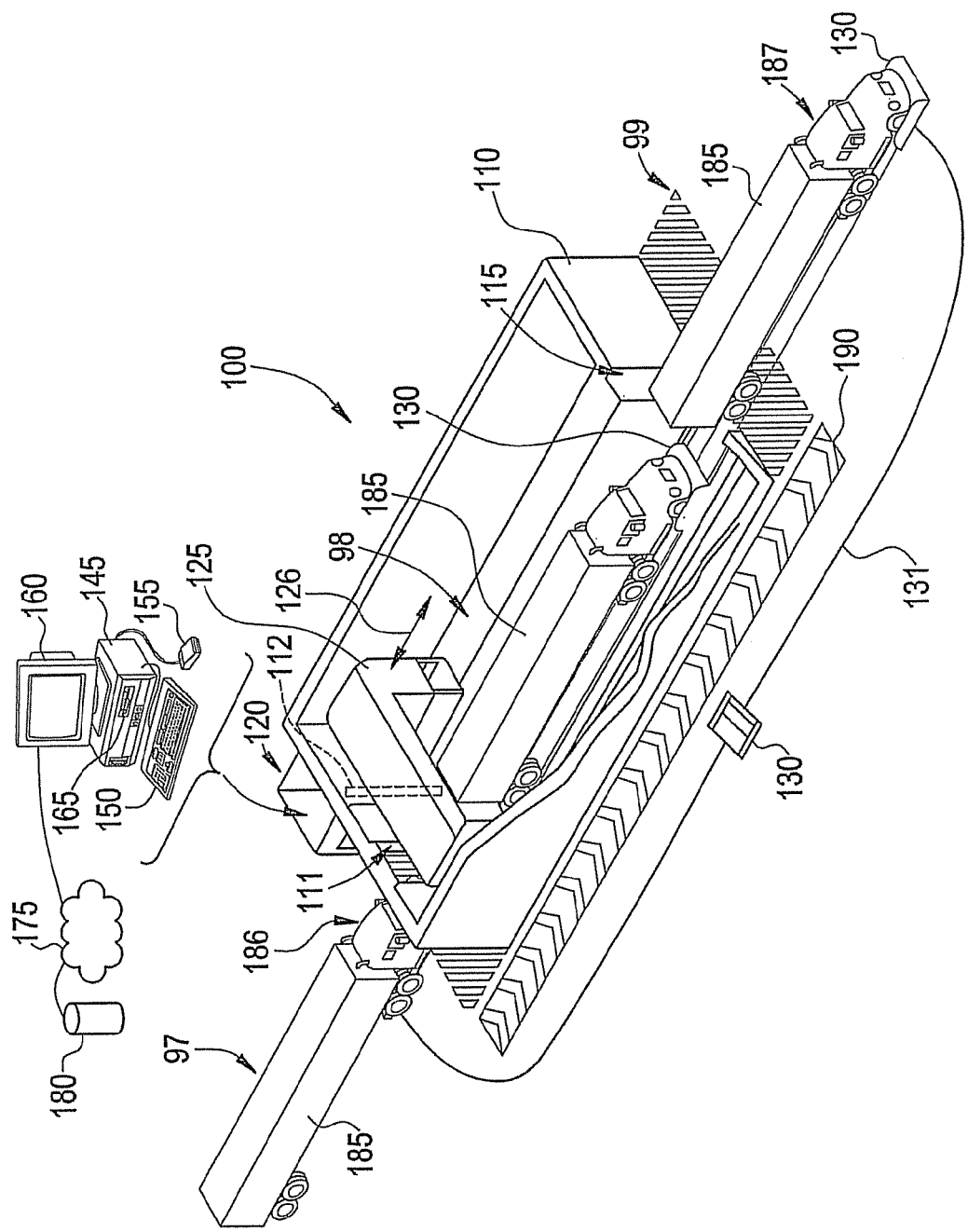
FIG. 1 depicts a perspective cut-away view of a inspection system in accordance with an embodiment of the invention.

Referring now to FIG. 1, a perspective cut-away view of an inspection system 100 is depicted. The inspection system 100 includes an enclosure 110, such as a building, to control, via shielding for example, a radiation level outside the building 110 resulting from the inspection process therein. In an embodiment, the building 110 includes an office 120, a support 125, such as a mobile gantry, also herein referred to as a gantry, and a set of truck-towing platforms 130. Within the office 120 is a processor 145, such as a computer, in signal communication with the mobile gantry 125 and the set of towing platforms 130. The processor 145 includes input devices 150, 155, such as a keyboard and mouse, an output device 160, such as a display screen, and a program storage device 165, such as a hard disk drive, for example. The program storage device 165 includes a program executing on the processor 145 for performing a method of inspection of a cargo container 185, which will be discussed in more detail below. The processor 145 may be in signal connection with a network 175, such as the Internet or an intranet, for example, that is in further connection with a database 180 that stores information associated with the inspection of cargo containers 185, also herein referred to as containers.

In an embodiment, the truck-towing platforms 130 are responsive to the processor to convey trucks 186 at least one of into, through, and out of the building 110. The utilization of at least one of the truck-towing platforms 130 and the mobile gantry 125 allow for a pipeline of the containers 185 for performing various processes in parallel with other processes, thereby preventing "waiting" periods that reduce the throughput. The use of the towing platforms 130 allows for increased throughput by eliminating a delay associated with an exit by a driver from the building 110. The mobile gantry 125 is responsive to control signals provided by the processor 145 to scan the container 185 at variable speed, forward and backward. The mobile gantry 125 further allows a more detailed, or "target" scan to be performed in response to possible discovery of items of interest, as will be described further below.

While an embodiment has been described having truck-towing platforms 130 to convey the trucks 186 into, through, and out of the building 110, it will be appreciated that the scope of the embodiment is not so limited, and that the embodiment will also apply to inspection systems 100 that include other vehicle movement arrangements, container support platforms to convey the cargo container 185 at least one of into, through, and out of the building 110 and to have the driver drive the truck at least one of into, through, and out of the building 110, for example.

Figure 2:
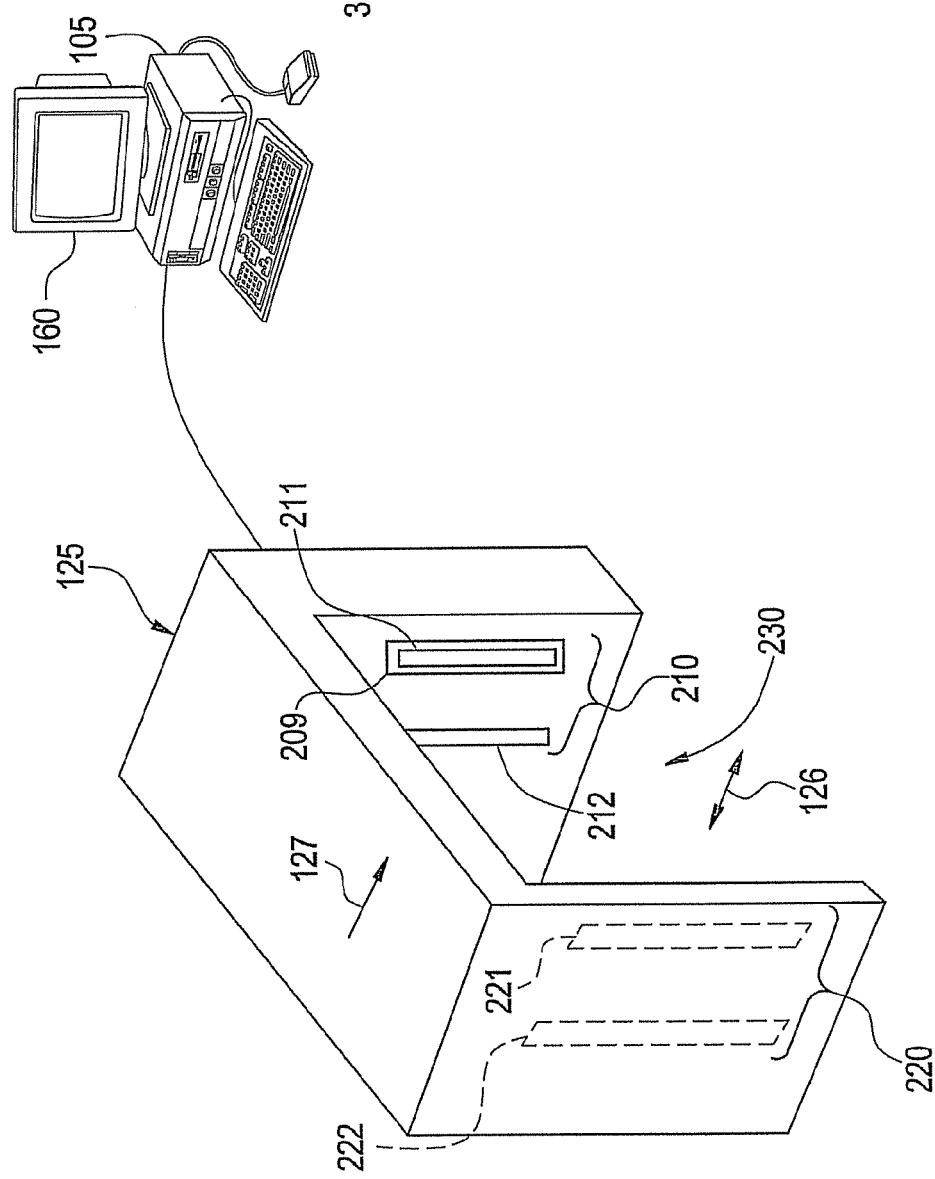
FIG. 2 depicts a perspective view of a mobile gantry in accordance with an embodiment of the invention.

Referring now to FIG. 2 in conjunction with FIG. 1, a top perspective view of the mobile gantry 125 is depicted. The mobile gantry 125 includes at least one radiation source 210, such as an x-ray source, and at least one radiation detector 220, such as an x-ray detector array. In an embodiment, the radiation source 210 includes a linear particle accelerator, or linac, to generate a beam of x-rays. The radiation source 210 and the radiation detector array 220 are mounted upon the mobile gantry 125. The radiation source 210 and radiation detector array 220 are opposingly disposed so as to be separated by an inspection cavity 230, dimensioned to allow movement of the cargo container 185 there through. In an exemplary embodiment, the cargo container 185 is disposed within the inspection cavity 230. The radiation source 210 is in signal communication with and responsive to the processor 145 to transmit a radiation beam directed toward the radiation detector 220 to pass through the container 185. The radiation beam passing through the container 185 is attenuated in response to material characteristics of contents within the container 185. After passing through and becoming attenuated by the container 185, the detector 220 receives the attenuated radiation beam. The detector 220 receives, or detects, the attenuated radiation beam and produces a set of electrical signals responsive to the intensity of the attenuated radiation beam. It will be appreciated that in response to motion of at least one of the container 185 and the mobile gantry 125, the set of electrical signals will vary along a length, as defined by a travel axis 126, of the cargo container 185. The set of electrical signals is made available to the processor 145, which executes a reconstruction program to interpret and represent the set of electrical signals as an image data set to be further analyzed, and displayed upon the display screen 160.

While an embodiment has been described having a linac to accelerate electrons to generate x-rays, it will be appreciated that the scope of the embodiment is not so limited, and that the embodiment will apply to other detection systems 100 that use other forms of radiation, such as protons impinging on one or more target materials to generate gamma ray radiation, and deuterons impinging on deuteriun, for example, to generate neutron radiation, for example.

In an embodiment, the processor 145 is receptive of and responsive to a screening (also herein referred to as an initial scan) that provides the set of electrical signals (also herein referred to as a screening detector signal) in response to transmission of a screening radiation beam, such as a screening x-ray beam. The transmission of the screening x-ray beam is along a length, also herein referred to as a screening portion, of the cargo container 185 and includes a corresponding screening scan rate along the screening portion. The processor 145, upon obtaining information from the initial scan, creates an image data set for the screening portion of the container 185 based upon the screening signals. The processor 145 analyzes the image data set to determine a likelihood of a presence of an item of interest, such as an item having at least one of high-Z material, and shielding material that may affect the ability of the screening x-ray beam from the source 210 to adequately penetrate the container 185 and be detected by the detector 220, for example. For example, the processor 145 may analyze the image data set to identify an unusual or unexpected density gradient, or the processor 145 may analyze the screening detector signal to determine if the screening detector signal is in excess of a threshold value. In response to the processor 145 determining a likelihood of a presence of items of interest within the container 185, the processor 145 identifies one or more target portions of the container 185 that are likely to contain the items of interest. The processor 145 will cause a transmission of a target radiation beam, such as a target x-ray beam. The transmission of the target x-ray beam is along a length, also herein referred to as a target portion, of the cargo container 185 and includes a corresponding target scan rate along the identified one or more target portions of the cargo container 185. In an embodiment, the screening portion represents an entire length of the container 185, and the one or more target portions represent lengths of portions of the container 185 that the processor 145 has determined have a likelihood of the presence of the items of interest. The target scan rate is different from the screening scan rate, to produce appropriate target electrical signals to increase detection decision accuracy. In an embodiment, the target scan rate is slower than the screening scan rate. As described above, the mobile gantry 125 is responsive to the processor 145 to translate along at least one of the screening portion and the identified target portion of the cargo container 185.

As used herein, the term "scan rate" will refer to the rate of displacement, or velocity, of the x-ray source 210 relative to the container 185. It will be appreciated that at least one of a particular screening scan rate and a particular target scan rate can be defined by at least one of a rate of motion in response to driving a truck 186, 187 in mechanical connection with the container 185, a rate of motion of the truck-towing platform 130, a rate of motion of the mobile gantry 125, and a rate of motion of a support platform upon which the cargo container 185 is disposed, for example.

Subsequent to transmission of the target x-ray beam, the processor 145 is receptive of and responsive to a set of target electrical signals provided by the detector 220 corresponding to the detected attenuated target x-ray beam. All image data set is created for the target portion of the container 185 based upon the target electrical signals. The processor 145 analyzes the image data set created from the target electrical signals to determine a presence or absence of the items of interest within the cargo container 185. The processor 145 is further configured to generate one of a first signal indicative of the presence of the item of interest or a second signal indicative of the absence of the item of interest. In an embodiment, in response to generation of the first signal indicative of the presence of high Z material, the cargo container 185 is inspected with an optional photo-fission interrogation to determine whether suspect item of interest is a fissile material.

In an embodiment, the gantry 125 includes a low energy radiation source 211, such as a low energy x-ray source, and a high energy radiation source 212, such as a high energy x-ray source also herein respectively referred to as a first and a second radiation source 211, 212. The first and second radiation source 211, 212 provide a set of multiple energy radiation beams, such as a set of multiple energy x-ray beams. In an embodiment, the set of multiple energy radiation beams is a dual-energy x-ray beam. The gantry 125 also includes two detectors 221, 222. The first x-ray source 211 generates one energy distribution of the multiple-energy x-ray beam and the second x-ray source 212 generates another energy distribution of the multiple-energy x-ray beam. The processor 145 is receptive of and responsive to the different electrical signals provided by the detectors 221, 222 in response to the detection of the multiple-energy x-ray beam from the x-ray sources 211, 212. The processor 145 provides an image of the container 185 contents via a technique known in the art as energy discrimination or dual-energy imaging. It will be appreciated that in response to a variation in material responses to different energy distributions, the energy discrimination imaging provided by the processor 145 distinguishes between different materials that may possess similar densities. This is in contrast to the capability to distinguish between the attenuation (resulting from differing densities) of different materials in single-energy x-ray imaging. At least one of the screening x-ray beam and the target x-ray beam include the multiple-energy radiation beam. As disclosed herein, the gantry 125 includes the first and second x-ray sources 211, 212 and provides the ability to identify the target portions of the container 185 that may require use of the target scan rate as necessary to provide adequate detection accuracy.

In another embodiment, the gantry 125 includes one radiation source 211 known in the art as an interlaced radiation source 211, such as an interlaced x-ray source 211, and the radiation detector 221. The interlaced x-ray source 211 is capable of alternating between emitting x-rays at more than one energy distribution in a very rapid fashion. The screening x-ray beam includes one scan of the screening portion of the container 185, emitting in rapid alternating fashion more than one energy distribution from the interlaced x-ray source 211, thereby providing the multiple-energy x-ray beam. It will be appreciated that the emission, in rapid alternating fashion, of the more than one energy distribution makes available to the processor 145 the necessary signals to develop a multiple-energy image of the contents of the container 185. In an embodiment, the target x-ray beam includes the set of multiple energy x-ray beams provided by the interlaced x-ray source 211.

An initial state is a truck 186 arriving at a loading position 97 at an entrance 111 to the building 110 (FIG. 1). The truck 186 is loaded into the truck-towing platform 130 (not visible in the depicted perspective) at the loading position 97, and a driver exits the truck 186 to walk toward a transport platform 190 disposed alongside the building 110, such as an escalator or a conveyor belt, for example. The truck 186 is towed to an inspection position 98 within the building 110 while identification of at least one of the container 185 and the truck 186 is made available to the processor 145 via at least one of the input devices 150, 155. In an embodiment, at least one of optical character recognition (OCR), radio frequency identification (RFID) or any other identification device technology are used to identify at least one of the container 185 and the truck 186. The identification of at least one of the container 185 and the truck 186 is saved, along with the inspection results in a record that corresponds to at least one of the truck 186 and the container 185 within the database 180. In response to disposition of the truck 186 at the inspection position 98 within the building 110, the processor 145 will provide a control signal to close doors at the entrance 111 and exit 115 of the building 110.

A container profile detector 112, such as a light curtain, in signal communication with the processor 145, is disposed proximate the entrance 111. In response to the motion of the truck 186 and the container 185, the light curtain 112 will make available to the processor 145 a signal representative of dimensions of a profile of the truck 186 and the container 185, and the processor 145 will send a control signal to automatically position the mobile gantry 125 along the travel axis 126 at the start of an x-ray scan, such as the rear the container 185, for example. In response to the processor 145, the x-ray source 210 will begin to generate an x-ray beam and the mobile gantry 125 will begin the scan of the container 185 while accelerating to a constant speed corresponding to the screening scan rate. In an embodiment, the mobile gantry 125 will accelerate to the screening scan rate of about three feet per second. The processor 145 will send a control signal to automatically stop the mobile gantry 125, such as in response to reaching the rear of the truck 186, as determined by the light curtain 112. While the scan is occurring, a second truck 186 is loaded onto another towing platform 130 at the loading position 97.

While an embodiment has been described having the rear of the container 185 as the start of the scan, it will be appreciated that the scope of the embodiment is not so limited, and that the embodiment will also apply to inspection systems 100 that scan in other directions, such as to start the scan at the front of the container 185, for example. Further, while an embodiment has been described to scan the container 185, it will be appreciated the scope of the embodiment is not so limited, and that the embodiment will also apply to inspection systems 100 that scan the truck 186 as well as the container 185, for example.

In an embodiment, the image data set is analyzed in real time to minimize the time to produce an alarm decision by the processor 145, such as in response to the processor 145 determining that the image data set created from the target signals indicate a likelihood of a presence of items of interest. Alternatively, the image data set of the container 185 is displayed upon the display screen 160 with a minimal delay resulting from the necessary time to process the image data set into a visual image, thereby allowing an operator to start inspecting the images before the scan is completed. The images are analyzed in real time to minimize the time to produce a "clear" decision that at least one of the truck 186 and the container 185 are absent of any item of interest, and to allow the truck 186 to leave.

In an embodiment, identified target portions of the container 185 that the processor 145 has determined may include the items of interest are presented to the operator via the display 160 of the processor 145. The operator can employ an image viewer to analyze a resulting image with a variety of image viewing and manipulation tools included with the reconstruction program executing on the processor 145. Operating procedures will instruct the operator to either clear the alarm based upon analysis of the images and release the truck 186, or to follow further alarming procedures, such as devaluing to remove the cargo from the container 185 for further inspection.

In an embodiment, a "standard" mode will include a complete scan of the entire truck 186 or container 185 via the screening x-ray beam transmitted by the radiation source 210, with the processor-determined result of the scan reported within about one second of the scan completion. If the "clear" decision is made, the doors at the entrance 111 and exit 115 are opened, and the truck 186 is conveyed by the truck-towing platform 130 out of the building 110 to a discharge position 99 while the next truck 186 waiting at the entry position 97 on the towing platform 130 is towed into the building 110 to the inspection position 98, and the process is repeated. The driver gets into the cleared truck 187 at the discharge position 99 and drives over the towing platform 130. The towing platform 130 is then transported to the entry position 97 outside the entrance 111 via a recirculating track 131.

In an embodiment of the "standard" mode, in response to one or more alarm decisions at the end of the complete scan, the processor 145 will automatically command the gantry 125 to rescan, via the target x-ray beam, the one or more target portions of the container 185 that included alarm conditions. The rescan will have the target scan rate. As described above, the processor 145 analyzes the image data set created from the target signals to determine if the image data set indicates a likelihood of a presence of items of interest, and provides the alarm decision with enhanced accuracy. The alarm decision may be one that is generated solely by the processor 145. Alternatively, the alarm decision may be recommended by the processor 145 and confirmed by the operator subsequent to further analysis of the images of the questioned target portions of the container 185. It will be appreciated that rescanning the target portions of the container 185 subsequent to finishing the complete scan will increase process times to assess the suspected target portions of the container 185. Other embodiments to reduce the process time are described below.

In another embodiment, the gantry 125 includes one radiation source 211 and one radiation detector 221. In response to the processor 145 determining that the electrical signal produced by the detector 221 in response to the screening x-ray beam has identified the target portion of the container 185 that may contain items of interest, the processor 145 commands the gantry 125 to stop and interrupt translation along the screening portion of the cargo container 185. The mobile gantry is responsive to go back to a beginning of the identified target portion of the container 185 and translate along the identified target portion of the cargo container 185 using the target x-ray beam, at the target scan rate required for the source 211 and detector 221 to yield the increased accuracy necessary to discriminate between items of interest and benign items. Subsequent to the questionable target portion having been scanned by the source 211 and detector 221 at the target scan rate, the processor 145 commands the gantry 125 to increase to the standard, higher speed, screening scan rate. It will be appreciated that for cases in which the one or more target portions are small compared to the length of the container, this will reduce the time required to provide a detailed examination of the contents of the container 185, as compared to the "standard" mode, because it eliminates the need to return the gantry 125 to the questionable target portion of the container 185 subsequent to the complete scan of the container 185.

In an embodiment, the gantry 125 includes two x-ray sources 211, 212 and two radiation detectors 221, 222. In response to the gantry 125 moving in a forward direction, as defined by direction line 127, it will be appreciated that the x-ray source 211 and radiation detector 221, (disposed opposite the source 211), are a leading source 211 and detector 221, also herein referred to as a screening radiation source and a screening radiation detector, to transmit and detect the screening x-ray beam. Similarly, the x-ray source 212 and radiation detector 222 (disposed opposite the source 212) are a trailing source 212 and detector 222, also herein referred to as a target radiation source and a target radiation detector, to transmit and detect the target x-ray beam. In an embodiment, the inspection system 100 operates in a "look-ahead" mode. In the "look-ahead" mode, in response to the processor 145 determining that the target portion of the container 185 that may contain items of interest using the screening x-ray beam, the gantry 125 is responsive to the processor 145 to interrupt translation along the screening portion and to translate along the identified target portion, including the target scan rate required for the target x-ray beam to yield the increased accuracy necessary to discriminate between items of interest and benign items. After the target portion has been scanned by the trailing source 212 and detector 222 at the target scan rate (with the target x-ray beam), the processor 145 commands the gantry 125 to resume translation along the screening portion (including the screening scan rate and the screening x-ray beam via the leading source 211 and detector 221). It will be appreciated that the "look-ahead" mode reduces the time required to provide a detailed examination of the contents of the container 185, as it eliminates the need to translate the gantry 125 backward to the beginning of the identified target portion of the container 185. In an exemplary embodiment, the leading source 211 is the interlaced multiple-energy source as described above, to reduce false alarms.

While an embodiment of the invention has been described having the gantry 125 moving in a forward direction to define a leading source and detector and a trailing source and detector, it will be appreciated that the scope of the embodiment is not so limited, and that the embodiment also applies to inspection systems 100 that use gantries that can move forward or backwards, for example.

Figure 3:
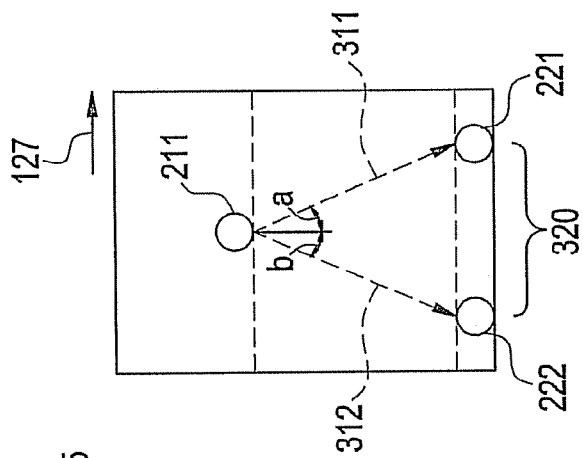
FIG. 3 depicts a top view of a mobile gantry in accordance with an embodiment of the invention.

Referring now to FIG. 3, in another embodiment the gantry 125 includes one x-ray source 211 and two radiation detectors 221, 222. In response to the gantry 125 moving in a forward direction, as defined by direction line 127, it will be appreciated that the radiation detector 221 is a leading detector 221, and the radiation detector 222 is a trailing detector 222. The x-ray source 211 projects the screening x-ray beam 311 at an angle represented by the variable "a" to the leading detector 221 and the target x-ray beam 312 at an angle represented by the variable "b" to the trailing detector 222, in a "modified look-ahead" mode. In the "modified look-ahead" mode, in response to the processor 145 determining that the leading detector 221 has identified the target portion of the container 185 that may contain items of interest using the screening x-ray beam, the gantry 125 is responsive to the processor 145 to interrupt translation along the screening portion and to translate along the identified target portion, including the target scan rate required for the target x-ray beam 312 (via the detector 222) to yield the increased accuracy necessary to discriminate between items of interest and benign items. After the target portion has been scanned by the trailing detector 222 at the target scan rate (with the target x-ray beam 312), the processor 145 commands the gantry 125 to resume translation along the screening portion, (including the screening scan rate via the screening x-ray beam 311 and the leading detector 221).

Due to the angular path difference, also known as parallax, of the screening and target x-ray beams 311, 312 the depth of the item to be re-examined is not known and the gantry 125 has to be repositioned backwards by a distance 320 that is related to the angle "a" and "b". Accordingly, the processor 145 identifies the target portion based upon a parallax angle defined by the x-ray source 211, the leading detector 221, and the trailing detector 222. This effect results in similar total rescanning time as the above embodiment that utilizes the gantry 125 with one source 211 and detector 221 to interrupt translation along the screening portion to go back to translate along the identified target portion, but requires the use of the additional detector 222.

As a result of data provided by observations to date, it is understood that on average about only thirty percent of containers 185 include contents that are likely to create an alarm condition, or require use of the target scan rate for one or more target portions of the container 185. In an embodiment, the system will operate in a "pre-scanning" mode. In the "pre-scanning" mode, the gantry 125 is positioned at the entrance 111, the truck 186 is driven into the building 110, and an intensity of the screening radiation beam, such as a reduced intensity x-ray beam, is less than the intensity of the of the target x-ray beam. In an embodiment, the gantry 125 includes a filter 209 disposed between the x-ray source 211 and the cargo container 185 to absorb energy and thereby reduce the intensity of the screening x-ray beam exiting the source 211. Use of the reduced intensity screening x-ray beam thereby provides a pre-scanning of the container 185. In an embodiment, the intensity is reduced such that it will not be necessary to close the doors of the building 110 for the containment of radiation and for the driver to exit the truck, and that neither the entrance 111, nor the location of the driver within the truck 186 will be subject to radiation levels that exceed any regulatory radiation exposure limits.

In an embodiment of the "pre-scanning" mode, the truck 185 is driven into the entrance 111, and x-ray source 211 is energized in response to the container 185 passing a plane corresponding to the reduced intensity screening x-ray beam emitted by the source 211, as determined by the light curtain 112. If no target portions that may include items of interest are identified, the truck 186 continues without stopping. In response to identification of one or more target portions, the truck 186 is commanded to stop. The driver then exits the truck 186, and doors to the building 110 are closed. In an embodiment using one x-ray source 211 with the filter 209, the filter 209 is removed from the x-ray source 211, and the target portions are inspected with a full intensity (non-filtered) target x-ray beam at the target scan rate, as described above. In another embodiment using two x-ray sources, the x-ray source 211 is the reduced intensity screening x-ray source 211, the detector 221 is a screening detector 221, the x-ray source 212 is a full intensity target x-ray source 212 that inspects the suspect areas with the full intensity target x-ray beam, and the detector 222 is a target detector 222. In another embodiment using two x-ray sources, the x-ray source 211 is used initially as a reduced intensity screening x-ray source 211 and the detector 221 is a screening detector 221. Subsequent to the pre-scan, the x-ray source 211 is restored to full intensity and both it and the full intensity x-ray source 212 are utilized to scan suspect areas with full intensity target x-ray beams, and the detectors 221 and 222 serve as target detectors. Additionally, in response to the processor 145 determining that the pre-screening inspection has identified several target portions, (or most of the container 185) as possibly having items of interest, the complete container 185 is scanned with the full intensity target x-ray beam. Once the scan is completed, and a "clear" decision is made, the doors to the building 110 are opened, and the driver returns to the truck 186 and proceeds to drive away. An advantage of this mode is that any humans that may be hidden within the container 185 are exposed to a smaller radiation dose as a result of the reduced intensity screening x-ray beam. In an embodiment, the processor 145 performs image analysis based on an advanced algorithm to indicate the presence of a human and provide an alarm to prevent irradiation with the full intensity x-ray beam.

In an embodiment, it may be desired to perform an inspection of the truck 186 and the container 185. In response to determining that the truck 186 and the container 185 are to be inspected, it is contemplated that use of the truck-towing platform 130 is preferred to avoid irradiation of the driver. In this mode, the truck 186 is conveyed into the building 110 and inspected via the reduced intensity screening x-ray beam as described above. An advantage of use of the truck-towing platform 130 is that in response to determining that the inspection with the full intensity target x-ray beam is necessary, the inspection system 100 will not have to wait for the driver to exit the truck 186, and therefore the effective scanning throughput is increased.

While an embodiment has been described as having the reduced intensity x-ray source 211, such as the screening x-ray source 211 disposed within the gantry 125 to provide the pre-scanning, it will be appreciated that the scope of the embodiment is not so limited, and that the embodiment also applies to inspection systems 100 that may have a radiation source disposed outside of the gantry and located at the building entrance 111, and that may or may not utilize the filter 209 to provide a radiation beam of appropriate intensity for the pre-scanning of at least one of the container 185 and the truck 186

In another embodiment, as an alternative to the use of the interlaced radiation sources described above, the gantry 125 includes one radiation detector 221 and one x-ray source 211 capable of emitting x-rays with more than one energy distribution in a non interlaced mode to provide the multiple-energy x-ray beam. In an embodiment, the screening x-ray beam includes at least two complete scans of the container 185 at the screening scan rate: the complete scan of the container 185 with one energy distribution followed by at least one other complete scan of the container 185 with a different energy distribution. Therefore, the screening x-ray beam provides to the processor 145 the necessary signals to develop the multiple-energy image of the contents of the container 185. As disclosed herein, an embodiment includes the ability to identify different portions of the container 185 that may require use of the screening and target scan rates as necessary to provide adequate detection accuracy for different portions of the container 185.

In another embodiment, the gantry 125 includes two x-ray sources 211, 212, at least one of which is an interlaced x-ray source 211, and two radiation detectors 221, 222. It has been observed that in some multiple-energy imaging applications, a noise ratio may be dominated by the low energy distribution. To provide improved signal statistics, it is contemplated to operate the at least one interlaced x-ray source 211 such that it generates at least two energy distributions of the multiple-energy x-ray beam, rapidly alternating between the at least two energy distributions. The other radiation source 212 is contemplated to operate such that it generates one of the at least two energy distributions. For example, during a scan of either the screening x-ray beam at the screening scan rate or the target x-ray beam at the target scan rate, the interlaced x-ray source 211 alternates between a 9 mega volt (MV) energy distribution and a 6 MV energy distribution and the other x-ray source 212 operates at a 6 MV energy distribution. As disclosed herein, an embodiment includes the ability to identify different portions of the container 185 that may require use of the screening and target scan rates as necessary to provide adequate detection accuracy for different portions of the container 185.

In an embodiment, the processor 145 is receptive of pre-inspection information to determine appropriate operation parameters of the inspection, such as the scan speed of the gantry 125, the intensity level of the at least one x-ray source 220, and the target portions of the container 185 that may require targeted inspection, for example. In an embodiment, the pre-inspection information includes the results of a pre-screening that may be performed by the inspection system 100, as described above, or by an additional assessment system. Additional examples of pre-inspection information regarding at least one of the container 185 and contents therein provided by a variety of pre-inspections include the result of a passive detection of radiation emission from the container 185 with portal monitors or handheld radiation monitors that detect the spontaneous decay of radioisotopes within the container, information provided on a shipping manifest, weight of the cargo container 185, exterior condition of the container 185, identity of a company responsible for shipping the container 185, and shipping origin of the cargo container 185, for example. Information provided on the shipping manifest may be relevant to determine expected traits of the container 185, such as an expected weight or density based upon the disclosed contents, for example. Similarly, the shipping origin, as well as any intermediate destinations, may indicate an increased (or decreased) possibility of items of interest within the container 185. The information regarding the company responsible for shipping the container 185 may for example, in conjunction with a history of previous inspection results for containers shipped by the same company, be relevant to determine companies that are expected to have a lesser or greater likelihood of shipping containers 185 including suspect object.

Accordingly, it will be appreciated that the inspection system 100 includes several operation scenarios that can provide various inspection throughputs. The inspection system 100 includes several implementation options including the building 110 that can scan one or more trucks, use of the truck-towing platforms 130, and scanning motion performed by at least one of the mobile gantry 125, the truck-towing platforms 130, and the driver of the truck 186. Embodiments also can include use of pre-inspection information.

Figure 4:
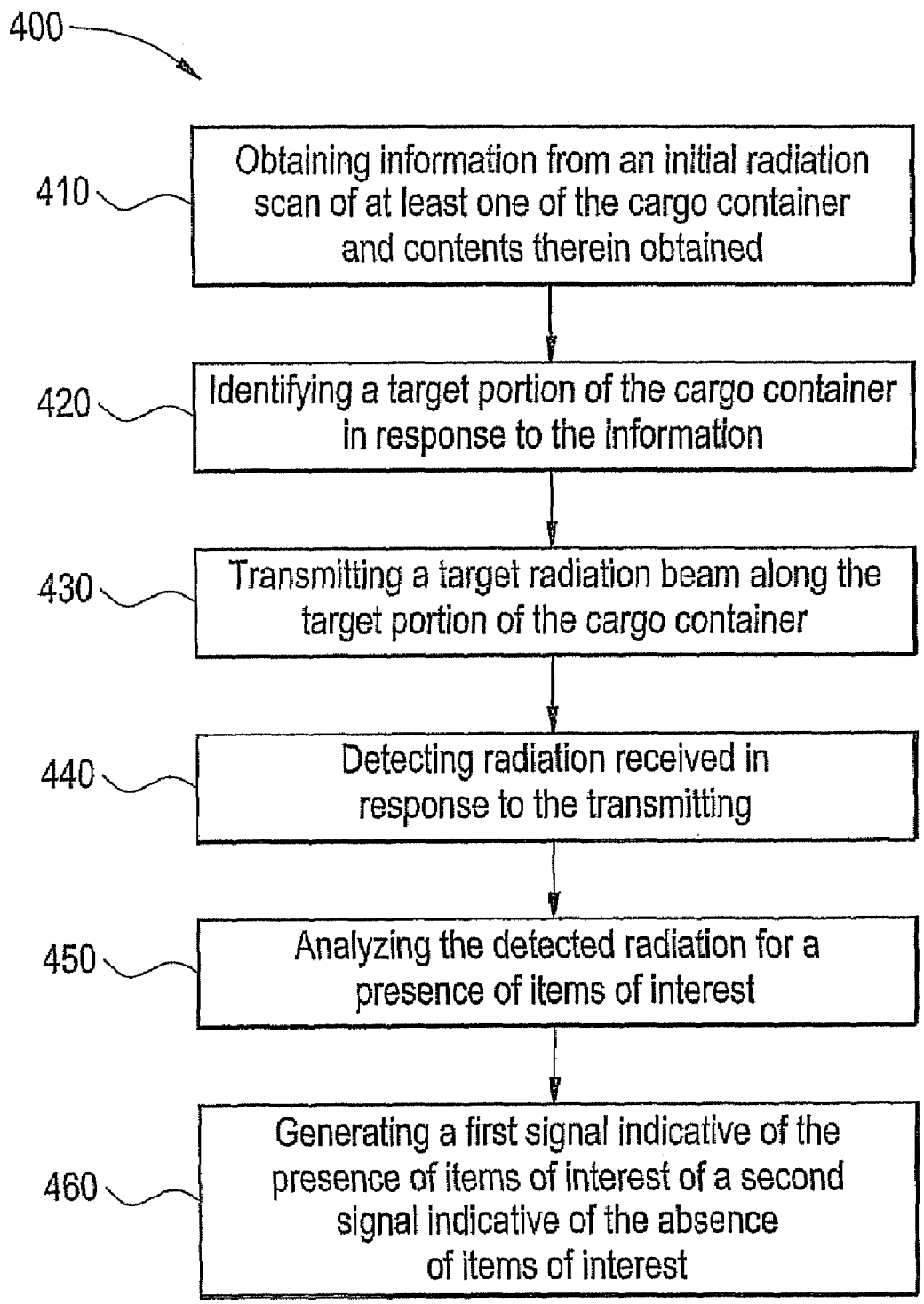
FIG. 4 depicts a flow chart of an embodiment of a method for detecting items of interest within a cargo container in accordance with an embodiment of the invention.

Referring now to FIG. 4, a flowchart of process steps for determining a presence of items of interest within a cargo container, such as the cargo container 185, by an inspection system, such as the inspection system 100, is depicted.

The process begins by obtaining at Step 410 information from the initial radiation scan of at least one of the cargo container 185 and contents therein. The process proceeds with identifying at Step 420 the target portion of the cargo container 185 in response to the information obtained, transmitting at Step 430 the target radiation beam along the target portion of the cargo container 185, detecting at Step 440 radiation received in response to the transmitted beam, analyzing at Step 450 the detected radiation for the presence of items of interest, and in response to the analyzing at Step 450, generating at Step 460 the first signal indicative of the presence of the items of interest, or generating the second signal indicative of the absence of the items of interest.

In an embodiment, the analyzing at Step 450 includes analyzing the detected radiation for the presence of high-Z material. In response to the generating at step 460, the signal indicative of the presence of high Z material, the method further includes inspecting the cargo container 185 using photo-fission interrogation to determine whether the item of interest is a fissile material.

In an embodiment, the obtaining information at Step 410 includes transmitting the screening radiation beam along the screening portion of the cargo container 185, the screening portion larger than the target portion, detecting radiation received in response to the transmitting the screening radiation beam, and analyzing the detected radiation received in response to the transmitting the screening radiation beam, to develop information regarding the initial radiation scan.

In an embodiment, the transmitting the target radiation beam at Step 430 and the transmitting the screening radiation beam include at least one of transmitting x-ray radiation, transmitting gamma ray radiation, and transmitting neutron radiation.

In an embodiment, at least one of the transmitting at Step 430 the target radiation beam and the transmitting the screening radiation beam include transmitting the set of multiple-energy radiation beams. In an embodiment, the transmitting the set of multiple-energy radiation beams includes transmitting the set of multiple-energy radiation beams via at least one interlaced radiation source 211. In another embodiment, the transmitting the set of multiple energy radiation beams via at least one interlaced radiation source 211 includes emitting the radiation beam including at least two different energy distributions via the at least one interlaced radiation source 211 and emitting another radiation beam including one of the at least two energy distributions via the other radiation source 212. In another embodiment, the transmitting the set of multiple-energy radiation beams includes transmitting the set of multiple-energy radiation beams via at least two non-interlaced radiation sources 211, 212.

In an embodiment, the transmitting the screening radiation beam includes transmitting the screening radiation beam along the screening portion of the cargo container 185 at the screening scan rate. Further, the transmitting at Step 430 the target radiation beam includes transmitting the target radiation beam along the identified target portion of the cargo container 185 at the target scan rate, the target scan rate being different, such as slower, than the screening scan rate.

In an embodiment, the screening radiation beam has a lower intensity than the target radiation beam, and the transmitting the screening x-ray beam includes transmitting the filtered screening x-ray beam having the lower intensity than the target x-ray beam.

In an embodiment, the transmitting the screening radiation beam having the lower intensity includes moving the cargo container 185 at the screening scan rate via at least one of the truck 186, the truck towing platform 130 and transmitting the screening radiation beam having the lower intensity via the stationary radiation source 211 along the screening portion of the cargo container 185.

An embodiment of the invention may be embodied in the form of computer-implemented processes and apparatuses for practicing those processes. Embodiments of the invention may also be embodied in the form of a computer program product having computer program code containing instructions embodied in tangible media, such as CD-ROMs, hard drives, USB (universal serial bus) drives, or any other computer readable storage medium, wherein, when the computer program code is loaded into and executed by a computer, the computer becomes an apparatus for practicing the invention. Embodiments of the invention also may be embodied in the form of computer program code, for example, whether stored in a storage medium, loaded into and/or executed by a computer, or transmitted over some transmission medium, such as over electrical wiring or cabling, through fiber optics, or via electromagnetic radiation, wherein when the computer program code is loaded into and executed by a computer, the computer becomes an apparatus for practicing the invention. When implemented on a general-purpose microprocessor, the computer program code segments configure the microprocessor to create specific logic circuits. A technical effect of the executable instructions is to increase a throughput of the inspection of cargo containers that may contain items of interest.

As disclosed, some embodiments of the invention may include some of the following advantages: the ability to detect items of interest within cargo containers; the ability to detect items of interest in the presence of materials intended to shield these items within cargo containers; the ability to identify portions of the container that may require a more thorough inspection; the ability to reduce total inspection time by performing a cargo container pre-scan with the same equipment to be used for a more thorough inspection; and the ability to reduce total inspection time using a low intensity pre-scanning.

While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best or only mode contemplated for carrying out this invention, but that the invention will include all embodiments falling within the scope of the appended claims. Also, in the drawings and the description, there have been disclosed exemplary embodiments of the invention and, although specific terms may have been employed, they are unless otherwise stated used in a generic and descriptive sense only and not for purposes of limitation, the scope of the invention therefore not being so limited. Moreover, the use of the terms first, second, etc. do not denote any order or importance, but rather the terms first, second, etc. are used to distinguish one element from another. Furthermore, the use of the terms a, an, etc. do not denote a limitation of quantity, but rather denote the presence of at least one of the referenced item.

What is claimed as new and desired to be protected by Letters Patent of the United States is:

1. A method of determining a presence of items of interest within a cargo container, the method comprising:
   obtaining information from an initial radiation scan of at least one of the cargo container and contents therein, the obtaining comprising:
      transmitting a screening radiation beam along a screening portion of the cargo container at a screening scan rate;
      detecting radiation received in response to the transmitting the screening radiation beam; and
      analyzing the detected radiation received in response to the transmitting the screening radiation beam to develop information regarding the initial radiation scan;
   identifying a target portion of the cargo container in response to the information obtained, wherein the screening portion is larger than the target portion;
   transmitting a target radiation beam along the target portion of the cargo container at a target scan rate, the target scan rate being different than the screening scan rate;
   detecting radiation received in response to the transmitting;
   analyzing the detected radiation for a presence of items of interest; and
   in response to the analyzing, generating a first signal indicative of the presence of the items of interest, or generating a second signal indicative of an absence of the items of interest.

2. The method of claim 1, wherein the analyzing comprises analyzing the detected radiation for a presence of high-Z material.

3. The method of claim 2, comprising inspecting the cargo container using photo-fission interrogation to determine whether the item of interest is a fissile material.

4. The method of claim 3, wherein said inspecting the cargo container is in response to generating a signal indicative of the presence of high-Z material.

5. The method of claim 1, wherein at least one of the transmitting the target radiation beam and the transmitting the screening radiation beam comprise at least one of:
   transmitting x-ray radiation;
   transmitting gamma ray radiation; and
   transmitting neutron radiation.

6. The method of claim 1, wherein at least one of the transmitting a target radiation beam and the transmitting a screening radiation beam comprise transmitting multiple-energy radiation beams.

7. The method of claim 6, wherein the transmitting multiple-energy radiation beams comprises transmitting multiple-energy radiation beams via at least one interlaced radiation source.

8. The method of claim 7, wherein the transmitting multiple energy radiation beams via at least one interlaced radiation source comprises:
   emitting a radiation beam comprising at least two different energy distributions via the at least one interlaced radiation source; and
   emitting another radiation beam comprising one of the at least two different energy distributions via another radiation source.

9. The method of claim 6, wherein the transmitting multiple-energy radiation beams comprises transmitting multiple-energy radiation beams via at least two non-interlaced radiation sources.

10. The method of claim 1, wherein the transmitting the screening radiation beam comprises transmitting the screening radiation beam having a lower intensity than the target radiation beam.

11. The method of claim 10, wherein the transmitting the screening radiation beam comprises transmitting a filtered screening radiation beam having the lower intensity than the target radiation beam.

12. The method of claim 10, wherein the transmitting the screening radiation beam comprises:
   moving the cargo container at the screening scan rate; and
   transmitting the screening radiation beam via a stationary radiation source.

13. A program storage device readable by a processor, the device embodying a program or instructions executable by the processor to perform the method of claim 1.

14. A cargo container inspection system comprising:
a processor;
a support comprising an inspection cavity dimensioned so as to surround the cargo container, the support in signal communication with the processor;
a radiation source disposed upon the support, the radiation source in signal communication with and responsive to the processor to transmit a radiation beam directed toward the cargo container; and
a radiation detector disposed upon the support opposite the radiation source, the radiation detector in signal communication with the processor to detect an attenuated radiation beam in response to the transmitted radiation beam passing though the cargo container;
wherein the processor, upon obtaining information from an initial radiation scan, identifies a target portion of the cargo container and causes transmission of a target radiation beam along the identified target portion; and
wherein the processor analyzes the attenuated radiation beam detected in response to the transmission of the target radiation beam to determine a presence or absence of items of interest within the cargo container and generates one of a first signal indicative of the presence of the items of interest, or a second signal indicative of an absence of the items of interest; and
wherein the processor is responsive to information from the initial radiation scan, the information comprising analysis of a screening detector signal in response to transmission of a screening radiation beam along a screening portion of the cargo container to identify the target portion, the screening portion larger than the target portion; and
wherein the transmission of the screening radiation beam along the screening portion of the cargo container comprises a screening scan rate, the transmission of the target radiation beam along the identified target portion of the cargo container comprises a target scan rate, and the target scan rate is different than the screening scan rate.

15. The system of claim 14 wherein the processor analyzes the attenuated radiation beam detected in response to the transmission of the target radiation beam to determine a presence or absence of high-Z material.

16. The system of claim 14, wherein at least one of the screening radiation beam and the target radiation beam comprise at least one of:
x-ray radiation;
gamma ray radiation; and
neutron radiation.

17. The system of claim 14, wherein:
at least one of the screening radiation beam and the target radiation beam is a multiple-energy radiation beam; and
the radiation source is an interlaced radiation source.

18. The system of claim 17, wherein the radiation source is a first interlaced radiation source to generate at least two energy distributions of the multiple-energy radiation beam, the system further comprising a second radiation source to generate one of the at least two energy distributions of the multiple-energy radiation beam.

19. The system of claim 14, wherein the radiation source is a first radiation source, the system further comprising:
a second radiation source;
wherein at least one of the screening radiation beam and the target radiation beam is a multiple-energy radiation beam; and
wherein the first radiation source generates one energy distribution of the multiple-energy x-ray beam and the second radiation source generates another energy distribution of the multiple-energy x-ray beam.

20. The system of claim 14, further comprising:
a truck-towing platform responsive to the processor;
wherein at least one of the screening scan rate and the target scan rate is defined by at least one of a rate of motion of a truck in mechanical connection with the cargo container, and a rate of motion of the truck-towing platform.

21. The system of claim 14, wherein:
the support is a mobile gantry responsive to the processor; and
at least one of the screening scan rate and the target scan rate is defined by a rate of motion of the mobile gantry.

22. The system of claim 21, wherein the mobile gantry is responsive to the processor to translate along the screening portion and the identified target portion of the cargo container.

23. The system of claim 22, wherein subsequent to identification of the target portion, the mobile gantry is responsive to the processor to interrupt translation along the screening portion to translate along the identified target portion.

24. The system of claim 23, wherein the radiation detector is a trailing radiation detector to detect the target radiation beam, the system further comprising a leading radiation detector to detect the screening radiation beam.

25. The system of claim 24, wherein the processor identifies the target portion based upon a parallax angle defined by the radiation source, the leading radiation detector, and the trailing radiation detector.

26. The system of claim 14, wherein an intensity of the screening radiation beam is less than the intensity of the target radiation beam.

27. The system of claim 26, further comprising a filter disposed between the radiation source and the cargo container to reduce the intensity of the screening radiation beam.

28. The system of claim 26, wherein the radiation source is a target radiation source to generate the target radiation beam and the radiation detector is a target radiation detector, the system further comprising:
a screening radiation source in signal communication with and responsive to the processor to transmit the screening radiation beam; and
a screening radiation detector disposed opposite the screening energy source, the screening radiation detector in signal communication with the processor to detect an attenuated screening radiation beam in response to the transmitted screening radiation beam passing though the cargo container.

29. The system of claim 28, wherein the screening radiation source and the screening radiation detector are disposed upon the support.

* * * * *

UNITED STATES PATENT AND TRADEMARK OFFICE
CERTIFICATE OF CORRECTION

PATENT NO. : 7,483,511 B2
APPLICATION NO. : 11/671042
DATED : January 27, 2009
INVENTOR(S) : Bendahan et al.

It is certified that error appears in the above-identified patent and that said Letters Patent is hereby corrected as shown below:

Column 4, Line 12, delete "deuteriun," and insert -- deuterium, --, therefor.

Column 5, Line 4, delete "All" and insert -- An --, therefor.

Column 7, Line 11, delete "devaluing" and insert -- devanning --, therefor.

Column 10, Line 1, delete "fall" and insert -- full --, therefor.

Signed and Sealed this

Twenty-fourth Day of March, 2009

JOHN DOLL
*Acting Director of the United States Patent and Trademark Office*